United States Patent [19]

Ratzlaff et al.

[11] Patent Number: 4,814,661
[45] Date of Patent: Mar. 21, 1989

[54] SYSTEMS FOR MEASUREMENT AND ANALYSIS OF FORCES EXERTED DURING HUMAN LOCOMOTION

[75] Inventors: Marc H. Ratzlaff, Moscow, Id.; Barrie D. Grant; John M. Frame, both of Pullman, Wash.

[73] Assignee: Washington State University Research Foundation, Inc., Pullman, Wash.

[21] Appl. No.: 113,816

[22] Filed: Oct. 26, 1987

Related U.S. Application Data

[63] Continuation-in-part of Ser. No. 866,875, May 23, 1986, Pat. No. 4,703,217.

[51] Int. Cl.$^4$ .............................................. H01L 41/08
[52] U.S. Cl. .................................... 310/328; 310/331; 310/338; 310/339; 310/319; 310/800; 73/172; 36/136
[58] Field of Search ........................ 310/328, 330-332, 310/338, 339, 800, 319; 119/29; 168/4, 17, 23, 24, 26; 340/500, 573, 665; 73/760, 432 R, 172; 36/136, 137

[56] References Cited

U.S. PATENT DOCUMENTS

| | | | |
|---|---|---|---|
| 3,582,691 | 6/1971 | Sonderegger | 310/338 X |
| 3,582,692 | 6/1971 | Palini | 310/330 |
| 4,158,117 | 6/1979 | Quilliam et al. | 310/800 X |
| 4,158,922 | 4/1979 | Dana, III | 36/137 |
| 4,402,147 | 9/1983 | Wu | 36/136 |
| 4,499,394 | 2/1985 | Koal | 310/330 |
| 4,510,704 | 4/1985 | Johnson | 36/136 |
| 4,660,305 | 4/1987 | Medler et al. | 36/139 |
| 4,703,217 | 10/1987 | Ratzlaff et al. | 310/330 X |

OTHER PUBLICATIONS

E. M. Hennig et al., "A Piezoelectric Method of Measuring the Vertical Contact Stress Beneath the Human Foot", J. Biomed. Eng., vol. 4, Jul. 1982, pp. 213–222.

S. Miyazaki et al., "Foot-Force Measuring Device for Clinical Assessment of Pathological Gait", Medical & Biological Engineering and Computing, Jul. 1978, pp. 429–435.

P. R. Cavanagh et al., "A New Device for the Measurement of Pressure Distribution Inside the Shoe", International Series on Biomechanics, vol. 4B, Biomechanics, 1983, pp. 1089–1096.

G. Gerliczy et al., "Solef PVDF Biaxially Oriented Piezo and Pyroelectric Films for Transducers", 1985 approximately.

Primary Examiner—Mark O. Budd
Attorney, Agent, or Firm—Wells, St. John & Roberts

[57] ABSTRACT

Systems including piezoelectric sensor elements advantageously mounted between supporting hard plastic material of various types or other mechanically similar materials. The sensor can further be supported by backup plate structures. Some backup plates show full shoe coverage and others show partial sole coverage. Detachable mounting formed by mechanically interengaging parts allow transducer inserts to be made in a modular manner for use in different sensor shoes or sensor insole pads, thus allowing many more patients to be analyzed and treated through use of the invention. Also disclosed is a digital charge signal integrator circuit.

55 Claims, 9 Drawing Sheets

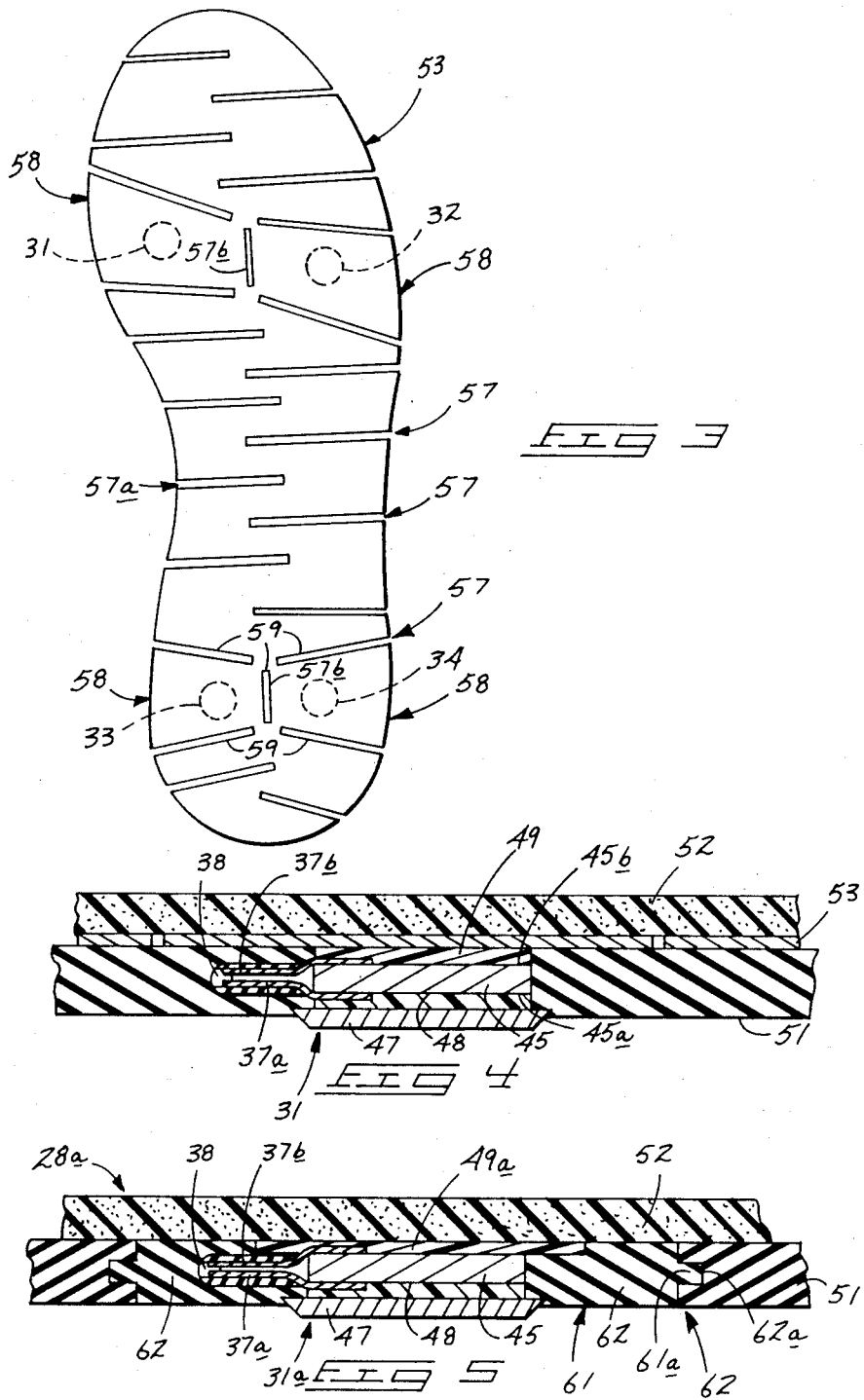

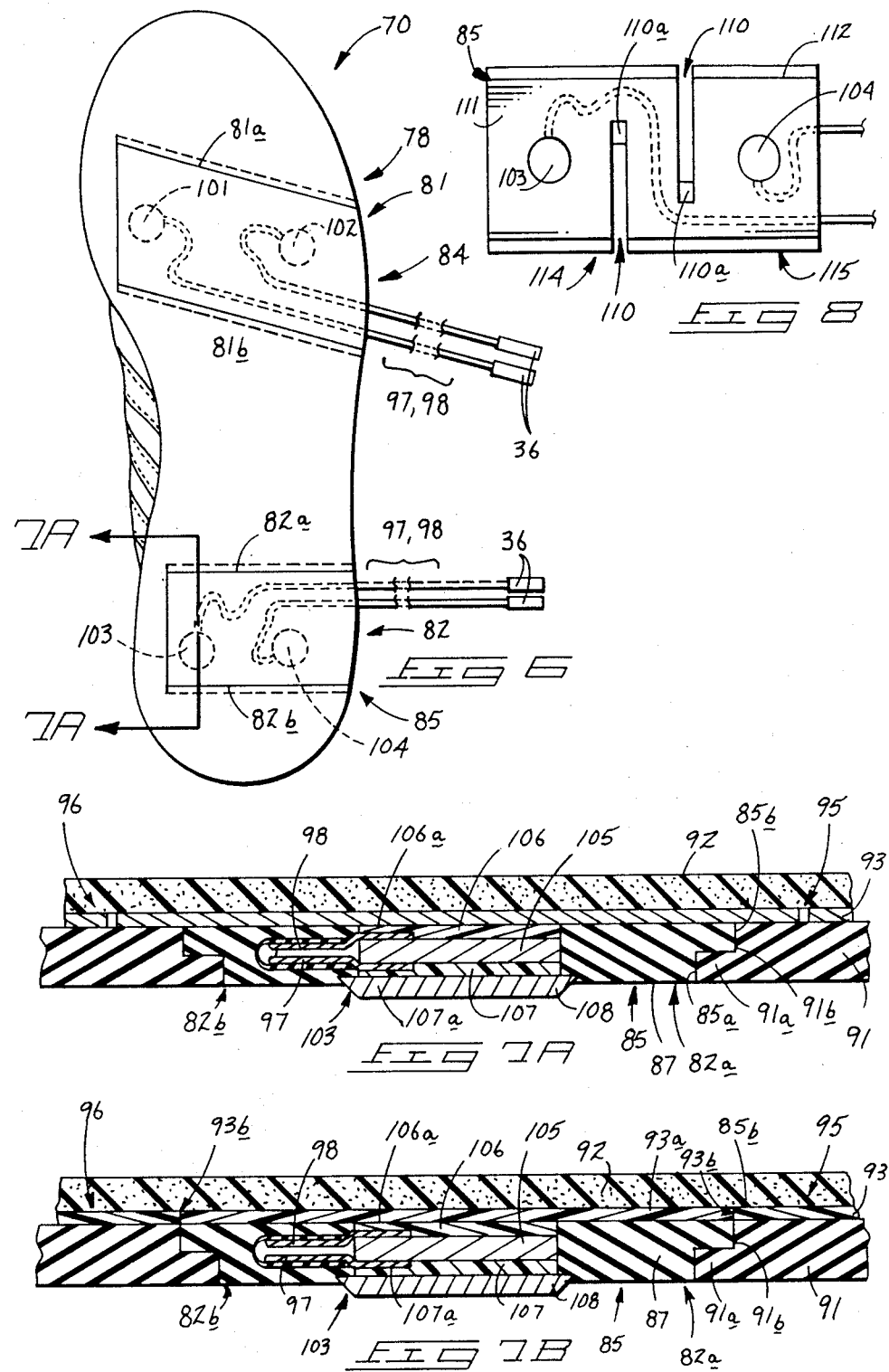

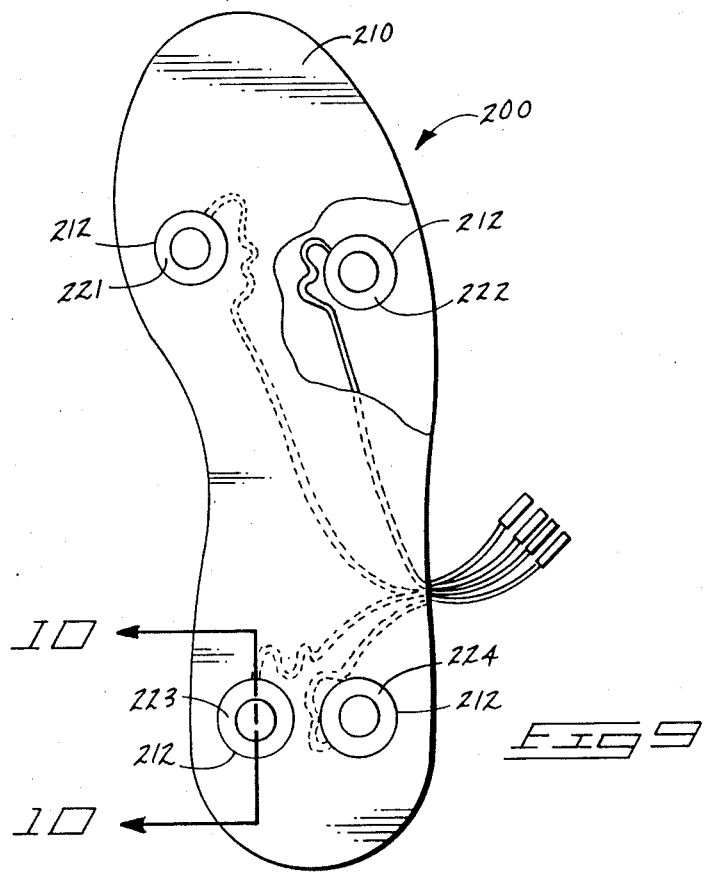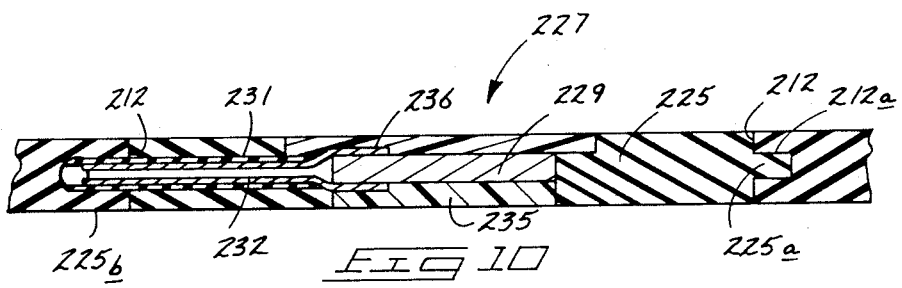

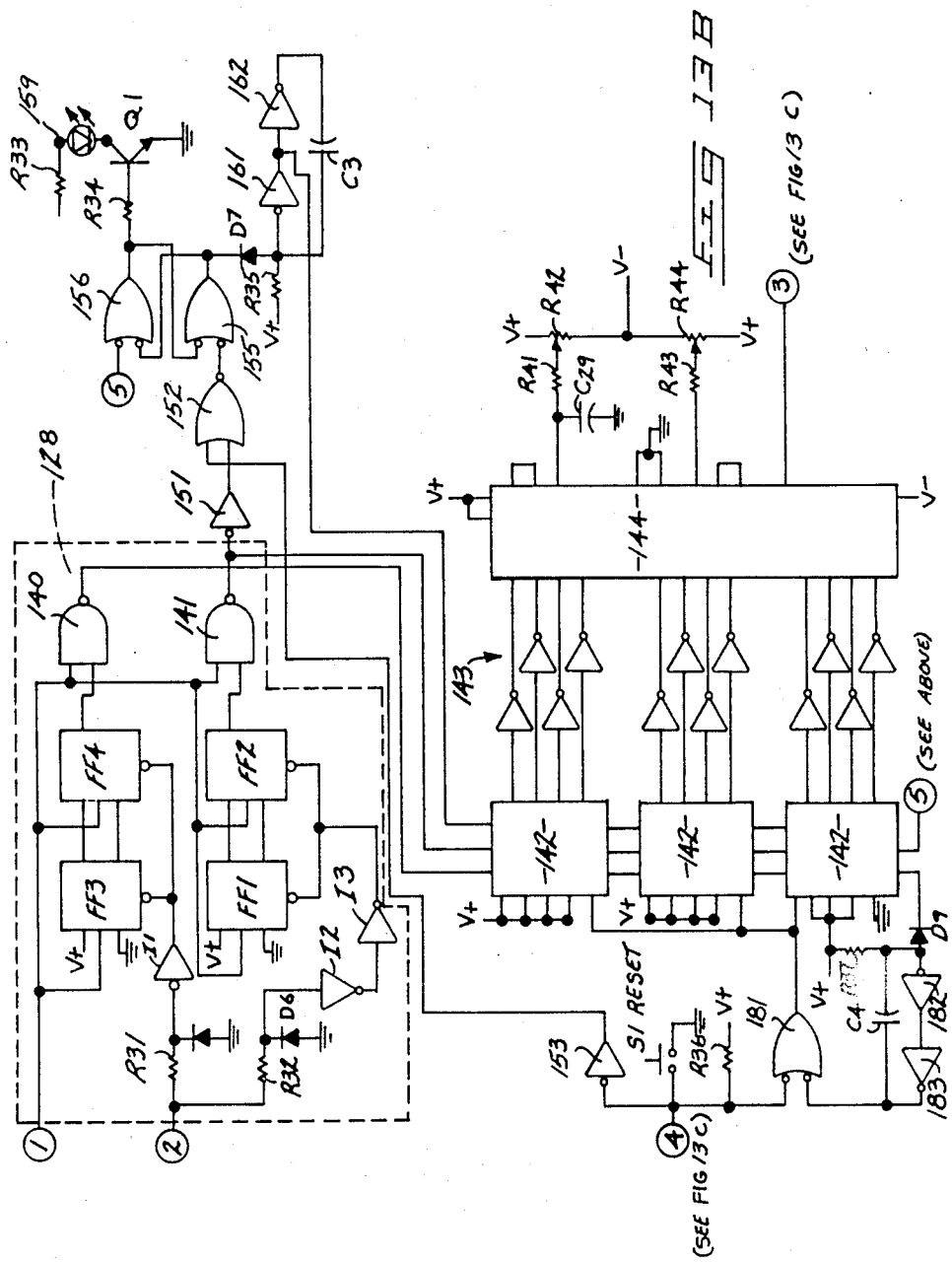

SYSTEMS FOR MEASUREMENT AND ANALYSIS OF FORCES EXERTED DURING HUMAN LOCOMOTION

This is a continuation-in-part of U.S. patent application Ser. No. 866,875, filed May 23, 1986; U.S. Pat. No. 4,703,217; and priority is claimed thereon.

TECHNICAL FIELD

The technical field of this invention includes systems for measurement and analysis of forces exerted by human feet during locomotion.

BACKGROUND OF THE INVENTION

There are a number of areas which benefit from having more accurate information concerning the types, distribution and characterization of forces applied to and by the human foot during human locomotion. Such information is relevant to the design and manufacture of shoes because of increasing sophistication in shoe design requiring a more clear indication of the types of forces applied, their distribution, and the shoe construction necessary in order to provide the proper design emphasis concerning factors such as force application, shock absorbtion, and energy distribution and dissipation concerns. This is particularly true in the design of high performance running footwear. The resiliency of the shoe and the manner of absorption and dissipation of energy have a significant effect upon the amount of energy that a runner must exert in order to travel at a certain speed. Shoes which have too high resiliency provide good shock absorbing capability and protect the foot but may also slow a runner because of the additional energy which is dissipated in the sole. However, other designs providing lower resiliency may minimize the amount of energy dissipation and produce more energy return to the human foot and hence improved speed or jumping capability.

Contact forces generated by human feet also are relevant to the design and construction of running surfaces such as indoor and outdoor track surfaces. As in shoe design, various track designs may differ in resiliency and other characteristics of the track surface. Improved techniques for gathering information on performance as a function of track resiliency, slope, surface smoothness or other parameters may facilitate the development of improved track surfaces and or better track materials and spacial configurations.

In addition to the mechanical aspects of the track and shoe, it may also be desirable to better understand the interaction action between the human foot structure and its interplay with the shoe and track in a coupled mechanical system so as to best design the shoe to accommodate the loading applied by the human foot. It is also desirable to create a match between the human foot and the shoe so that forces are applied in a manner which is attuned to the particular goal or balance of goals. For instance, in long distance running it may be most desirable to design a shoe so that human foot-shoe-ground interaction minimizes pressure points and alleviates the physical stress placed on the feet. Alternatively, it may be desirable in middle distance and sprint racing to have shoes which are designed to provide greatest speed capability with somewhat less concern about the stress level which may be applied by and to the foot since substantial mechanical injury to the skin and sole tissues of the foot are less likely to occur during relatively short periods of higher speed running.

Orthopedic surgeons and doctors are also in need of systems which provide relatively quantitative indications of stride variations, timing and associated foot contact pressures and forces. This information may be useful to the orthopedic professional for analysis of bone implants, joint ailments, muscular deficiencies, improper running or walking techniques and other medical or training related phenomena which can be studied, analyzed and/or inidicated as a result of information concerning foot contact forces, their timing and distribution.

Previously it has been common to employ force plates for determination of contact forces by a human foot. Force plates utilize various types of sensors which indicate the total vertical, and in some cases lateral forces, applied by the human foot as it contacts the force plate. Unfortunately, force plates have several disadvantages. The force plates are typically mounted in a fixed position and the human subject walks or runs over the force plates. Accordingly, it is necessary for the subject to properly space and time his or her stride so as to apply foot contact at an appropriate point on the force plate. This necessarily causes the subject to vary his or her stride to provide such results. This prevents unrestrained motion leads to force information, and any stride information, which is altered by the conscious effort of the subject to coordinate foot fall patterns and timing so as to comply with the force plate scheme. Such systems are not suitable for analyzing foot force and pressure information during free locomotion and under a variety of different gaits.

An insole has been developed for use in measuring stress distribution on the plantar surfaces of the human foot during walking and running by Hennig, Cavanaugh, Albert and MacMillan. The Hennig et al. device utilized 499 different piezoelectric ceramic transducers. The transducers each were approximately 4.78 millimeters square by 2 millimeters thick and constructed of lead zirconate titanate crystals imbedded in a 3 to 4 millimeter thick layer of highly resilient silicone rubber that apparently was molded about the 499 ceramic transducers to produce a flexible array which was designed to be impervious to moisture and electrically insulative between the different transducer elements. The transducers had silver electrodes which were diffusion bonded to their major surfaces. The transducers were laid out in a square array substantially covering the plantar surfaces of an insole. The insole was installed in a specially designed shoe and connected to a computer system via hardwired connections which severely limited mobility and prevented unrestrained motion from being analyzed.

The Hennig et al. force measurement system and transducer array did not provide means for evenly distributing the force applied across each individual transducer crystal. Instead variations of force due to varying elasticity and thicknesses of the tissue of the foot and insole produced contact stresses which were nonuniform over the surface of each individual transducer. Such variations in the applied stress or other causes reduced the charge output generated by the transducer thus leading to output signals which had relatively lower signal-to-noise ratios than are achievable with the present invention.

The Hennig et al. device also suffers from severe limitations in terms of the cost. Construction of insoles according to their teaching requires use of nearly 500 elements in one insole design and twice that amount for simultaneous monitoring of both feet, as required for stride analysis. The cost of construction of such devices is many thousands of dollars for each insole due to the numerous transducers used. The transducers are also embedded in a molded silicone rubber insole which necessarily is especially adapted to a particular foot size both with respect to the layout of the transducer array and the size of the silicone rubber insole itself. This necessitates construction of numerous different insoles in order to test a broad range of subjects. Because of the financial burden imposed by this type of construction, many research projects have not been able to utilize the Hennig system in testing of numerous different subjects having various shoe sizes.

Therefore, there remains a need for transducer assemblies and foot force detection systems which provide accurate foot force detection in an economical manner and can be adapted for sensing and recording information from a variety of different subjects without utilizing specially constructed shoes for each different foot size. There also remains a need for a system which is relatively portable and capable of measuring human foot contact forces during unrestrained motion.

BRIEF DESCRIPTION OF THE DRAWINGS

Preferred embodiments of the invention are shown in the drawings. A brief description of the drawings is given below.

FIG. 3 is a bottom view of a back-up plate which is included in the shoe of FIG. 1.

FIG. 4 is a cross-sectional view taken along line 4—4 of FIG. 2 showing mounting of a sensor assembly in the shoe.

FIG. 5 is a cross-sectional view of an alternative construction which may be used in a shoe similar to that shown in FIG. 1.

FIG. 6 is a bottom view of a further alternative embodiment foot force detection assembly according to this invention incorporated into a shoe similar to the shoe shown in FIG. 1.

FIG. 7A is a cross-sectional view taken along line 7A—7A of FIG. 6.

FIG. 7B is a cross-sectional view of an alternative embodiment in a view similar to FIG. 7A;

FIG. 8 is an enlarged bottom view showing the insert shown in FIG. 7A in isolation.

FIG. 9 is a bottom view of a force detection insole according to this invention.

FIG. 10 is a cross-sectional view taken along line 10—10 of the insole shown in FIG. 9.

FIGS. 13A-13C are electronic schematic diagrams showing a preferred signal processing and digital integration circuit useful in systems according to this invention.

DETAILED DESCRIPTION OF THE PREFERRED EMBODIMENT

The following disclosure of the invention is submitted in compliance with the constitutional purpose of the Patent Laws "to promote the progress of science and useful arts" (Article 1, Section 8).

Figure 1:
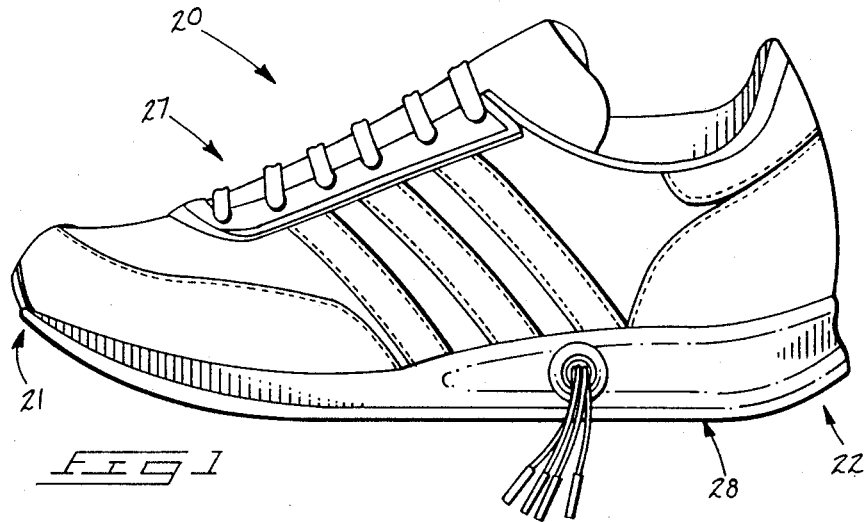
FIG. 1 is a side elevational view of a shoe adapted to function as a force detector for use in foot force detection systems according to this invention.

FIG. 1 shows a foot force sensor shoe 20 according to this invention. Sensor shoe 20 has a toe 21 and heel 22. Shoe 20 further has a medial side (inside) 24 and a lateral (outside) 25. The uppers 27 of the shoe are connected to a sole assembly 28 which has been specially adapted to sense the force applied by the human foot.

Sole assembly 28 includes an outer sole 51, an inner sole 52, a reinforcing backup plate 53, and a plurality of transducer or sensor assemblies 31-34. Outer sole 51 can be made from any suitable sole material such as a variety of elastomeric compounds commonly used in sport shoes. Rubber is one suitable material for outer sole 51. Inner sole 52 can be made from a variety of relatively elastic or spongy materials which provide greater comfort for the sensor shoe wearer. Inner soles made from foamed natural rubber or synthetic elastomeric materials are suitable for inner sole 52.

Figure 2:
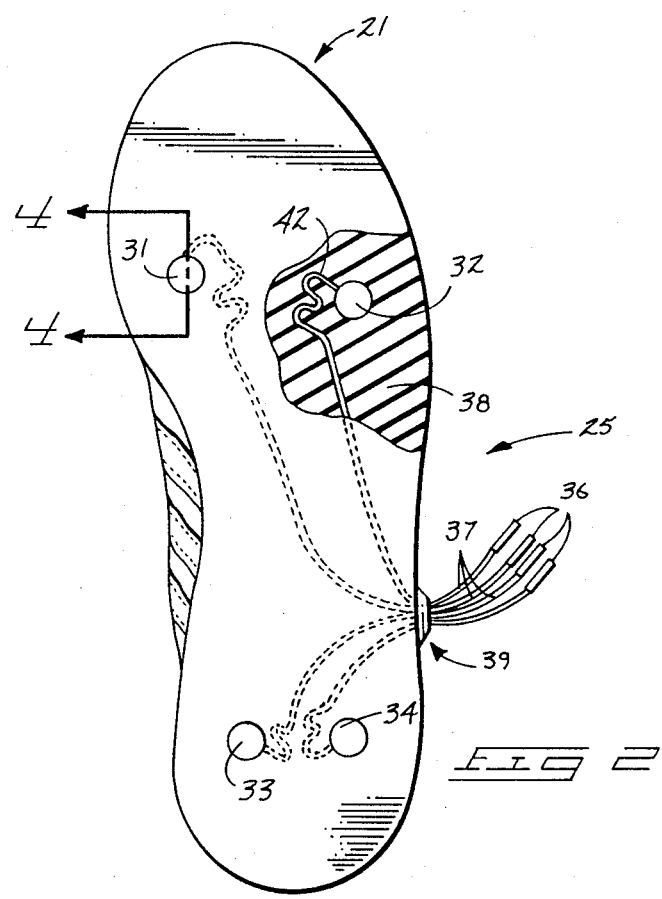
FIG. 2 is a bottom view of the shoe shown in FIG. 1.

FIG. 2 shows four sensor assemblies 31-34. Sensor assemblies 31 and 32 are positioned beneath the ball of the foot at medial and lateral positions, respectively. Sensor assemblies 33 and 34 are positioned at medial and lateral positions in the heel of the shoe, respectively. Each sensor assembly is connected by two wires to a suitable detachable connector 36. The sensor connection wires 37 are preferably coaxial in order to reduce reception of extraneous electronic noise. Sensor connection wires 37 are advantageously run through small tubular conduits 38 which extend between a connection wire conduit opening 39 and each of the individual sensors 31-34. The sensor connection wire conduits 38 are each preferably provided with switchbacks or convolutions 42 which provide flexibility in the conduit and connecting wire to prevent breakage of the wires or connections to the sensor assemblies. The specific form of the convolutions or switchbacks can be substantially altered while providing the flexibility needed to accommodate flexing and distortion of the sole assembly 28 during walking, running or other movement.

FIG. 4 shows a preferred form of construction for sensor assemblies 31-34. The specific sensor assembly description given below with respect to FIG. 4 shows sensor assembly 31; however, the remaining sensor assemblies 32-34 are similarly constructed. Sensor assembly 31 includes a suitable piezoelectric element 45. Piezoelectric element 45 is preferably a ceramic piezoelectric disk having poled faces 45a and 45b. The poled faces preferably are coated with a very thin metallic or other conductive coating which enhances conduction of the charge generated when the piezoelectric elements are forced, normal to the substantially parallel poled surfaces, such as under compression. The conductively coated poled surfaces 45a and 45b provide surfaces to which the sensor connection wires 37 may be soldered or adhesively bonded using solder or suitable electrically conductive adhesives. FIG. 4 shows a positive connection wire 37a connected to the lower or ground-directed poled surface 45a. FIG. 4 also shows a negative connection wire 37b connected to the negative or foot directed side 45b of sensor element 45.

Sensor assembly 31 also preferably includes a ground contacting cap 47 and a pair of nonconductive insulating disks 49 and 48 positioned above and below sensor element 45, respectively. Insulating disks 48 and 49 are preferably constructed of relatively rigid dielectric material such as a suitably stiff plastic having relatively low compressional resiliency as defined by the range of known plastics. A preferred form of sensor assembly utilizes a polycarbonate such as manufactured under the trademark Lexan for both upper and lower disks 48 and 49. The relative strength and rigidity of the polycarbonate insulating disks further is important in providing sufficient support and alignment for the sensor elements so as to enhance application of a relatively normal force to the surface of the piezoelectric element. These support disks further provide for relatively uniform loading across the entire poled faces of the piezoelectric element. This configuration and structure has been found significant in generating accurate and repeatable measurements of foot force applied to the transducers with a greater signal-to-noise ratio than the prior art. It is further noteworthy that the dielectric support disks preferably provide some ability to deform in order to better serve the intended purpose of both insulating and distributing a unified load to both faces of the piezoelectric element. Relatively hard and rigid materials such as most metals and ceramics are not suitable for this purpose since they do not adequately distribute and equalize the load. Such relatively inelastic materials also tend to create relatively concentrated loading at particular sensor assemblies versus sensor assemblies using more elastic and plastic materials which tend to increase the resiliency of the assemblyies which allows better indication of actual force at each assembly rather than concentrating the applied force on one or more sensors as might occur with very rigid assemblies. The sensor assemblies are preferably less resilient than the outer or contacting sole material 51. It should further be noted that although some resiliency is desired in the sensor assembly, it is not desirable to use materials which are considered elastomerically soft or highly resilient in the ordinary usage of such terms. Material such as sponge rubber and a variety of relatively soft foamed natural rubber and elastic materials are not suitable in most instances for the insulatory support disks 48 and 49. This unsuitability is apparently because they do not provide sufficient bending strength for proper structural support and distribution of stress so as to provide relatively uniform loading over both the ground-directed and foot-directed faces of the sensor element 45, and hence produce a relatively weaker charge flow signal.

FIG. 3 shows a plan view of backup plate 53 in isolation. The relative positions of the sensor assemblies 31-34 are shown in phantom. Sensor assemblies 31-34 can be adhesively bonded or mechanically connected to backup plate 53. Alternatively, the sensor assemblies can be mechanically coupled such as by being held in position by molding the assemblies into outer sole 51 with mechanical positioning of the sensor assemblies adjacent to appropriate portions of backup plate 53. In a preferred embodiment the sensor assemblies are each adhesively bonded with ground contacting face piece 47, insulatory support disks 48 and 49, sensor element 45 and backup plate 53 forming a single assembly using adhesive bonds. The relatively stiff but somewhat resilient plastics preferably used for support disks 48 and 49 also allow such a composite assembly to adequately comply with compressive stresses to prevent sensor breakage while producing a highly efficient mechanical coupling and good signal generation.

Sensor assemblies 31-34 are connected to backup plate 53 at stress isolated sections 58. The transducer mounting stress isolation sections 58 are preferably integrally connected with the adjacent portions of the backup plate in a manner which minimizes transfer of bending stresses to the portions of the stress isolation sections which mount the transducer assemblies. FIG. 3 shows one preferred construction for the backup plate which utilizes a number of flexion joints 57 in the form of stress isolation slots 59 which extend entirely through the thickness of the backup plate and allow the transducer mounting sections to flex with respect to adjacent portions of the backup plate. It is alternatively possible for stress isolation sections to be totally or partially defined by relatively thin webs (see 110a in FIG. 8) in lieu of the stress isolation slots. Such webs concentrate stress and allow bending to occur at the flexion joints formed thereby.

Backup plate 53 is also advantageously provided with a number of additional flexion joints 57 which are advantageously formed by further stress isolation slots 59 or other suitable means for providing flexibility. Such additional flexion joints allow the backup plate to flex and contort in a manner similar to the elastomeric soles which are typically used on sporting or other types of shoes. Backup plate 53 is specially constructed by the use of numerous flexion joints to provide sufficient compliance so as to properly comply with the types of forces experienced during wear of a normal shoe having similar sole and insole construction. It also allows the shoe to be sufficiently compliant so as to provide similar response to a normal shoe in both walking and running so that the wearer perceives the shoe is comfortable and normal gait or stride is achieved. This in turn allows more normal foot fall patterns and more accurate analysis of the foot force magnitude and timing information to be obtained.

It is further noteworthy that the backup plate 53 includes both transverse flexion joints such as shown at 57a and longitudinal flexion joints such as included between the two adjacent transducer mounting stress isolation sections 58 at joints 57b. Backup plate 53 is advantageously made of aluminum or other suitable metal having a thickness of 1-10 millimeters (mm), more preferably 2-5 mm. Backup plate 53 can also be constructed of relatively rigid polymeric materials or composite materials having suitable stiffness and limited compressive resiliency.

FIG. 5 shows an alternative sole force sensor mounting construction which can be used in a shoe similar to shoe 20. The sole design and transducer mounting assembly shown in FIG. 5 does not utilize the relatively rigid backup plate 53. Instead, the piezoelectric sensor assembly 31a is mounted in an insert 61 which advantageously is adapted to mechanically interengage with the outer sole 51 or other parts of the sole assembly 28a. A preferred form of mechanical interengagement is by using a tongue and groove joint 62. Tongue and groove joint 62 includes a tongue portion 61a which is shown formed on the insert 61. A groove 62a is shown formed in the outer sole 51 and is sized to receive the tongue portion 61a.

The transducer insert 61 is formed using a transducer assembly 31a which is molded or otherwise formed or embedded into a suitable insert ring 62. Insert piece or ring 62 is preferably circularly annular and adapted for mechanical engagement with other portions of the sole assembly 28a. Sole assembly 28a is similar to sole assembly 28 but provided with transducer insert receptacles to provide relatively fixed locations for receiving the transducer assemblies.

It is also noteworthy that the sensor assembly 31a is modified as shown in FIG. 5 to include an oversized insulating support disk 49a which is approximately 1½ times or greater the diameter or other breadth size of the piezoelectric sensing element 45. Upper insulating disk 49a serves as a backup plate means providing sufficient bending rigidity so as to function as a stress distributing element which helps to assure uniform loading of the sensor 45. Backup insulating disk 49a is flexibly connected to remaining portions of the sole to provide a flexion joint(s) such as by bonding with insert piece 62. Alternatively the transducer assemblies can be permanently bonded to the outer and or inner soles.

FIGS. 6 and 7A show an alternative embodiment force sensor shoe constructed according to this invention. Shoe 70 is similar in basic construction to shoe 20 described above and includes a sole assembly 78. Sole assembly 78 has been specially constructed to provide transducer insert receptacles 81 and 82 which are at the ball and heel sections of the shoe sole, respectively. The transducer insert receptacles 81 and 82 are constructed so as to allow mounting of transducer mounting inserts 84 and 85, respectively. The transducer inserts and receptacles are advantageously adapted in the coordinated fashion so as to allow slidable or other insertion and mechanical retention of the transducer inserts therein. As shown in FIGS. 6 and 7A the inserts are made with approximately parallel front and back side edges 81a and 81b, 82a and 82b, respectively, for front and back inserts 81 and 82. FIG. 7A shows the construction of rear transducer insert 85 in greater detail. Similar construction is also used for front transducer insert 84 except that the front insert is somewhat parallelepiped whereas heel insert 85 is substantially rectangular. Rear transducer insert 85 includes a rear transducer insert piece 87 which is specially configured to allow the slidable insertion of insert 85. As shown, the insert includes a relatively narrower outer portion 85a and a relatively broader or extending recessed portion 85b. The outer sole 91 is specially configured with an outer extension or overhanging lip 91a and enlarged recess 91b which is sized to receive the complementary structure formed along the front and back edges of insert 85.

Shoe 70 is advantageously provided with a substantially full sole backup plate 93 which is interposed between the outer sole 91 and inner sole 92. The backup plate is constructed so as to provide flexion joints 95 and 96 which essentially isolate the portions of the backup plate which apply force to the transducer or sensor assembles 101-104.

Sensor assembly 101 is constructed in a manner substantially similar to transducer assembly 31 described with respect to FIG. 4 above. Sensor assembly 101 is not mechanically or adhesively bonded to backup plate 93 but instead relies upon the close proximity of the transducer to backup plate 93 as provided by the interengagement along the slidable joints 82a and 82b. More specifically, transducer assembly 101 includes a piezoelectric element 105 which is preferably a poled ceramic piezoelectric crystal such as described above as 45. The upper and lower surfaces of piezoelectric element 105 are insulated using upper and lower insulatory support disks 106 and 107. Disks 106 and 107 are preferably constructed of a relatively stiff yet plastic and somewhat resilient material such as the polycarbonate described above. Insulatory disks 106 and 107 are advantageously adhered to the poled faces of transducer element 105 using a suitable adhesive. Insulatory pieces 106 and 107 are preferably provided with grooves or slots 106a and 107a which provide space for routing and connection of the sensor wires 97 and 98. A stainless steel contacting face piece 108 is advantageously adhered or otherwise connected to the lower insulatory disk 107. The insert ring 85 is preferably made from a dielectric elastic material such as polyurethane, epoxy and other flexible nonconductive materials.

FIG. 7B shows a further alternative sensor assembly mounting construction according to this invention. The mounting is substantially the same as shown in FIG. 7A except the sole assembly is not provided with a continuous backup plate but instead uses a discontinuous backup plate or partial backup plates 93a which are attached to form part of the transducer inserts 85a. Flexion joints are provided between the sole and insert at backup plate discontinuities 93b which isolate the inserts which are otherwise as described with respect to insert 85.

FIG. 8 shows that the preferred transducer inserts 84 and 85 are provided with flexion joints 110 which extend longitudinally inward over 50 percent of the way between the front and back edges 82a and 82b. Flexion joints 110 are provided with grooved portions which transform into webs 110a at the dead ends. Flexion joints 110 allow the stress isolated sections 114 and 115 which mount medial and lateral sensor assemblies 103 and 104 to flex independently of one another and prevent application of undesired bending stresses to the transducer sensing elements.

FIG. 9 shows a preferred embodiment force detection insole made according to this invention. Insole 200 includes a foot pad portion 210 which is shaped and sized to fit within an appropriate shoe of a human subject (not shown). Insole portion 210 can be constructed of any suitable relatively elastic and resilient material such as rubber, foamed polymer materials, or other suitable relatively sheet-like material designed to be received within the shoe beneath the foot of the wearer. Such insoles are preferably 3-12 mm in thickness.

Force sensing insole 200 is further adapted for its specific purpose by including a plurality of transducer mounting means 212 at desired points on the insole. As shown, insole 200 is adapted with four transducer mounting receptacles 212 at medial and lateral positions at both the ball and heel of the foot. Receptacles 212 are adapted to receive four transducer insert assemblies 221-224 which are adapted to be received at the medial ball, lateral ball, medial heel, and lateral heel positions in insole 200. Transducer inserts 221-224 are preferably constructed as interchangeable modules for convenience in use and ease of manufacture assembly, and maintenance.

FIG. 10 shows cross-sectional detail of insert 221 which is also representative of the remaining transducer inserts 222-223. Insert 221 includes an annular insert pad portion 225 which is advantageously constructed with a suitable mechanical fastening system which allows it to be detachably removed from receptacle 212. As shown, receptacle 212 is adapted by including a interengagement groove 212a which receives an interlocking tongue portion 225a of insert pad 225. Insert pad 225 is preferably made from a resilient material such as relatively high density closed cell polymer foam or other resilient resin materials.

Transducer insert 221 also includes a transducer assembly 227 which includes a suitable piezoelectric sensor element 229. Sensor element 229 is preferably coated with a conductive coating along the poled upper and lower faces in a manner similar to that described above with respect to other transducer assemblies. Sensor connection wires 231 and 232 are bonded to the coated, poled surfaces of the piezoelectric element to receive current generated by the piezoelectric element 229. The transducer assembly 227 also includes a first insulating disk 235 and second insulating disk 236. Insulating disk 235 is preferably made in a shape which is the same as of or very similar to the piezoelectric element 229. As shown, both are circular disks. Second disk 236 serves as a backup plate and is preferably constructed with a diameter which is approximately 1½ times or greater than the diameter of the piezoelectric element 229. Both first and second insulating pieces 235 and 236 are preferably routed or grooved in order to provide passages through which the connecting wires 231 and 232 can extend. The wires are preferably molded into the material forming annular insert portion 225 and extend through a perimetric wall (225b) of the insert. Insole 200 is preferably further adapted by including small tubular conduits which extend between the outer lateral surfaces of the insole and to receptacles 212. The conductive wires 231 and 232 are fed through the conduits and extend out through the lateral side of the insole for connection to suitable electronic circuitry, such as described herein.

Preferred insoles according to this invention can also be constructed using an insole design which is substantially the same as the sole designs shown in FIGS. 6, 7A and 7B except that the inserts do not include a backup plate as shown in FIGS. 6, 7A, 7B and 8. Instead the backup plate means is provided by oversized backup support disks such as shown and described with respect to FIG. 10. Such alternative insole designs do however allow use of replaceable transducer insert units thereby allowing the same transducer inserts to be used with a variety of insole pads having varying shoe sizes and proportions.

The apparatuses described above are advantageously used to measure vertical forces applied by the foot through the shoe structure. Such forces can also be termed the perpendicular or normal contact forces. The normal contact forces may not always be vertical. The ability of the poled ceramic piezoelectric elements to selectively detect forces normal to the poled surfaces allows the selective measurement of such forces without confusion from lateral forces which vary widely depending on the steepness, uphill or downhill direction and other walking and running variables.

The output signals from the piezoelectric elements, such as 45, 103 and 229, produce an electrical charge flow or current which is directly proportional to the change in force applied across poled faces of these elements and substantially normal thereto. This relationship between change in charge and change in force can be further developed mathematically to produce the relationship that the instantaneous force is equal to the integral of the piezoelectric element current over time from a time when applied force was zero or some other reference point. Changes in force can be both positive (increases) and negative (decreases) with associated positive and negative current associated therewith. Thus, at any point in time an integral of the current over time since a zero or other reference point will indicate the existing force upon the piezoelectric sensor elements.

Figure 12:
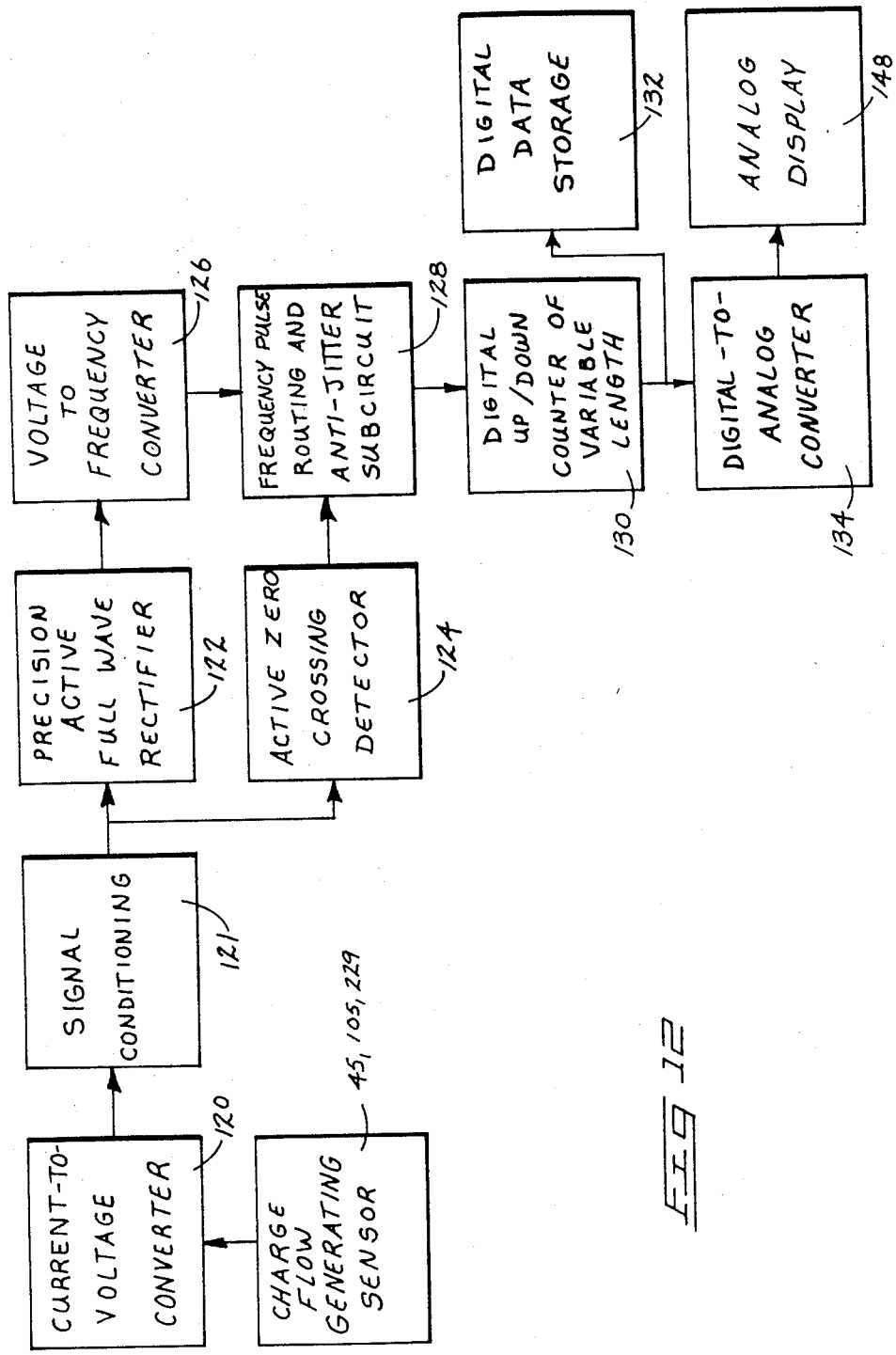
FIG. 12 is a block diagram showing functional portions of a preferred signal processing and digital integration circuit advantageously used in systems according to this invention.

FIG. 12 shows a preferred signal processing and digital force integrator according to this invention. FIG. 12 indicates that the output current from a piezoelectric element or other charge flow generating sensor is input into a current-to-voltage converter 120. The voltage varying output produced by current-to-voltage converter 120 is input into a precision active full wave rectifier 122 which produces an absolute value for the instantaneous voltage signal value produced by converter 120. The output from current-to-voltage converter 120 also is input to an active zero crossing detector 124 which provides an output signal indicating whether the voltage signal output from converter 120 is positive or negative.

The absolute value output from precision active full wave rectifier 122 is input to a voltage-to-frequency converter 126. The output signal from voltage-to-frequency converter 126 is a stream of pulses or otherwise a time varying signal having a frequency rate which is linearly related to the absolute value voltage signal input thereto.

The output from voltage-to-frequency converter 126 is either directly input to a digital up/down counter or more preferably input through a frequency pulse routing and anti-jitter subcircuit 128. Subcircuit 128 preferably routes the absolute value voltage derived pulses from voltage-to-frequency converter 126 using the positive or negative indication produced by active zero crossing detector 124. Pulses are thus routed to digital up/down counter 130 to produce either a counting up or counting down integration.

Anti-jitter portions of subcircuit 128 cause the subcircuit to maintain routing either positive or negative until there are at least two pulses from voltage-to-frequency converter 126 having a changed polarity. This feature prevents unnecessary vacillation of the counter when force or other sensory input is not changing. Output from digital up/down counter 130 can be directly recorded in any suitable digital data storage device 132. Alternatively or additionally, the output from up/down counter 130 can be input to a digital-to-analog converter 134 for any desired analytical processing, recording or for use in an analog or other display 148 indicating force or pressure in real time.

Figure 13A:
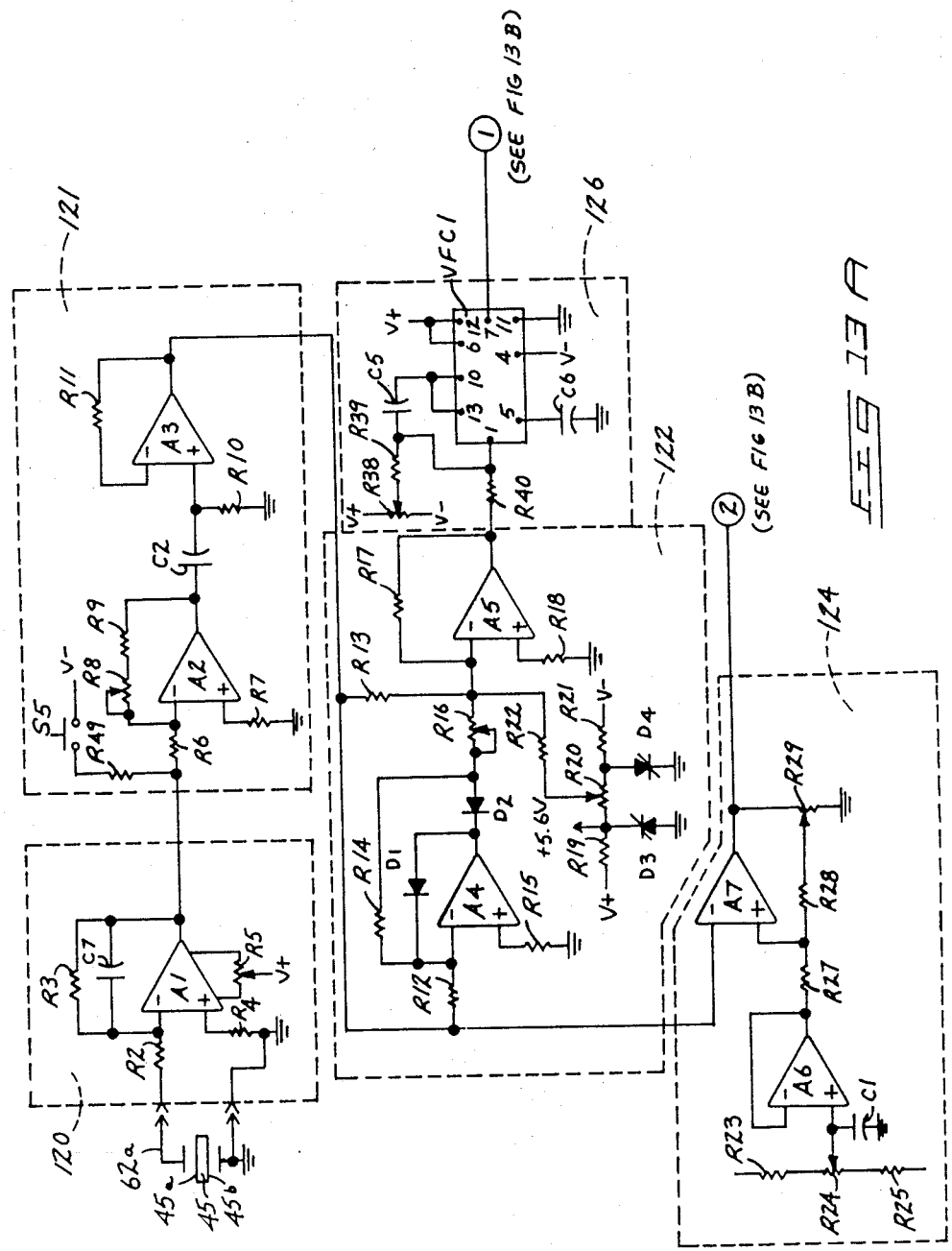
Figure 13C:
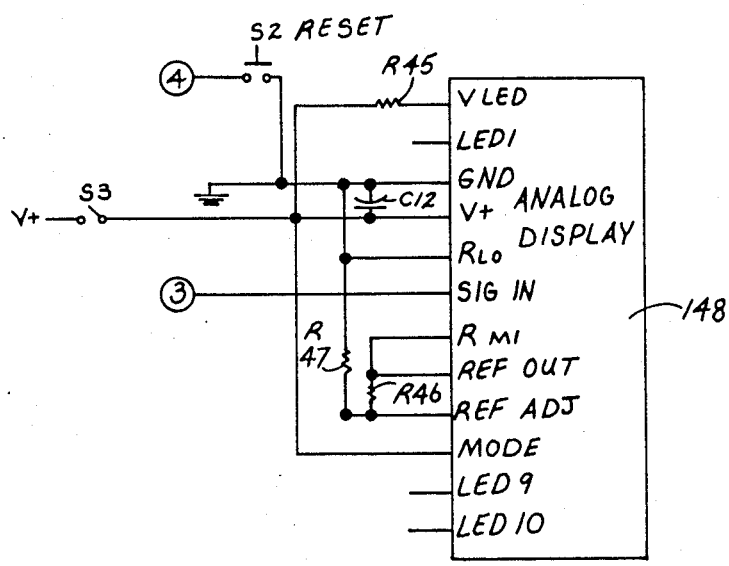

FIGS. 13A-13C show more specifically the electronic circuit components which are advantageously used in carrying out the signal processing and digital force integrator circuit more generally described with respect to FIG. 12.

FIG. 13A shows a piezoelectric element 45 having a positive pole 45a and negative pole 45b. Negative pole 45b is advantageously grounded. Positive pole 45a is connected to the minus terminal of operational amplifier A1 through resistor R2. A preferred value for resistor R2 and values for other components are shown in TABLE I below. Operational amplifier A1 is connected with the plus input grounded through resistor R4. Potentiometer R5 is connected to a positive general voltage input, V+, which is advantageously +9 volts. General negative voltage supply, V−, is similarly −9 volts. Potentiometer R5 is used to balance the operation of high impedance operational amplifier A1.

Feedback is provided from the output of A1 through parallel resistor R3 and capacitor C7 to the minus input thereof. The value of R3 can advantageously be 1 megaohm although the specific resistance is selected depending upon the type of sensor from which the charge flow or current signal is originating. The capacitance of capacitor C7 also varies depending upon the sensor used. Capacitance values for C7 may typically vary between 20 picofarads and 0.01 microfarad. Operational amplifier A1 and the related components discussed form current-to-voltage converter 120.

FIG. 13A also shows operational amplifiers A2 and A3. The function of operational amplifiers A2 and A3 is to amplify and condition the voltage varying signal produced by amplifier A1. The output from A1 is connected to the minus terminal of amplifier A2 through resistor R6. A test switch S5 is used to supply negative voltage V− through resistor R49 for diagnostic purposes. The feedback loop from the output of A2 includes resistor R9 and potentiometer R8. The plus input to amplifier A2 is connected to ground through resistor R7.

The output from A2 is passed through capacitor C2 and onto the plus input of operational amplifier A3. The plus input of operational amplifier A3 is also grounded through resistor R10. The feedback loop from the output of amplifier A3 is passed through resistor R11 to the minus input terminal thereof.

The conditioned voltage varying output from amplifier A3 is input to both active zero crossing detector 124 and precision active full wave rectifier 122. Precision active full wave rectifier 122 includes operational amplifiers A4 and A5 appropriately connected as shown with related components. The output of A3 is input through resistor R12 to the minus terminal of amplifier A4. The plus terminal of amplifier A4 is grounded through resistor R15. The output from amplifier A4 is connected to the anode of rectifying diode D1. The cathode of diode D1 is connected to the minus input of A4. The output of A4 is also connected to the cathode of rectifying diode D2. The anode of diode D2 is connected to a potentiometer R16 and to the minus terminal of amplifier A4 through resistor R14. The output from potentiometer R16 is connected to the minus terminal of operational amplifier A5.

The minus terminal of amplifier A5 is also connected to the output from A3 via resistor R13. The minus terminal of operational amplifier A5 is also connected to resistor R22. The plus terminal of operational amplifier A5 is connected to ground through resistor R18. A feedback loop from the output of amplifier A5 is passed through resistor R17 to the minus terminal thereof.

Resistor R22 is also connected to a voltage supply subcircuit, including potentiometer R20, and zener diodes D3 and D4. Zener diodes D3 and D4 are connected with the anode and cathode thereof to ground, respectively. The opposite ends of diodes D3 and D4 are connected to opposing ends of the winding of potentiometer R20. A resistor R19 is connected to the cathode of D3 and to a +9 volt power supply. The opposite end of resistor R19 is connected to the V+ power supply. The anode of zener diode D4 is also connected to resistor R21. The opposite end of resistor R21 is connected to the minus 9 volt power supply.

The output from operational amplifier A5 is the absolute value of the voltage signal output from amplifier A3. This absolute value voltage varying signal is input to a voltage-to-frequency converter 126. Converter 126 includes integrated circuit VFC1 which receives the input signal via resistor R40. A wide variety of voltage-to-frequency converters are available and usable with this invention. Voltage-to-frequency converters having the fastest response time and widest dynamic range are preferred. The voltage-to-frequency converter is connected to positive and negative 9 or other appropriate voltage power supplies through potentiometer R38, resistor R39 and capacitor C5 as shown in FIG. 16A. Capacitor C6 is connected between VFC1 and ground. Other power supply connections can be made as indicated in FIG. 13A. The specific configuration used will depend upon the particular voltage-to-frequency converter included in systems built according to this invention.

The voltage signal from amplifier A3 is also input to operational amplifier A7 forming a part of active zero crossing detector 124. Active zero crossing detector 124 identifies whether the voltage signal from amplifier A3 is negative or positive and then provides an output from amplifier A7 which is indicative of whether the voltage signal is positive or negative.

Active zero crossng detector 124 includes operational amplifier A6 which is connected to the wiper of potentiometer R24 and to capacitor C1. The opposite plate of capacitor C1 is grounded. One side of the winding of potentiometer R24 is connected through resistor R23 to a +5.6 volt power supply. The opposite end of the winding is connected through resistor R25 to a −5.6 volt power supply. The output from amplifier A6 is fed back to the minus terminal thereof. A resistor R27 is connected between the output of amplifier A6 and the plus terminal of A7. The minus input to amplifier A7 is from the output of amplifier A3. The output of amplifier A7 is connected to the winding of R29, the opposite end of which is grounded. The wiper of potentiometer R29 is connected through resistor R28 back to the plus input terminal of amplifier A7.

The output from amplifier A7 is preferably connected to the frequency pulse routing and anti-jitter subcircuit 128 using resistors R31 and R32 of FIG. 13B. The opposite end of resistor R31 is connected to the cathode of diode D5. The anode of D5 is grounded. The opposite end of resistor R32 is connected to the cathode of diode D6. The anode of diode D6 is grounded. The output signal from amplifier A7 is passed through resistor R31 and on to inverter-amplifier I1. The output from amplifier A7 is also passed through resistor R32 and on the inverter-amplifiers I2 and I3 and further on to two J-K flip-flops FF1 and FF2 configured as a two step shift resister. Flip-flops FF3 and FF4 are connected to the output from inverter I1 in a similar fashion, also creating a two step shift register.

The output from voltage-to-frequency converter VFC1 is communicated to flip-flops FF1–FF4 as shown in FIG. 13B to perform two step shift registration. The two outputs from the shift registers formed by flip-flops FF1–FF4 are input to inverting AND gates 140 and 141. The configuration of flip-flops, inverters, and resistors just described comprise the frequency pulse routing and anti-jitter subcircuit 128.

Frequency varying pulses from VFC1 are routed through inverting AND gate 140 when the voltage signal from amplifier A3 is positive, thus indicating the need for a positive count. When the voltage signal is negative from A3, the resulting frequency varying signal from voltage-to-frequency converter VFC1 is passed out through inverting AND gate 141 in order to produce a down or minus count. The outputs from inverting AND gates 140 and 141 are connected to three four bit up/down counters 142 which are cascaded to provide twelve bit counting capability. The output from counters 142 is a digital presentation indicating the integral of the sensor current on a real time basis. Digital output is taken from the outputs from up/down conters 142 shown at the righthand side thereof in FIG. 13B.

A digital-to-analog converter 144 is connected to the digital outputs from cascaded up/down counters 142 through inverters 143 as shown in FIG. 13B. Digital-to-analog converter 144 also is preferably connected to capacitor C29, resistor R41 and R43, potentiometers R42 and R44, and the negative and positive 9 volt power supplies as indicated in FIG. 13B in order to provide zero adjustment and span adjustments for the digital-to-analog converter. A variety of suitable digital-to-analog converters are useful in this invention.

The output of digital-to-analog converter 144 can be connected to a suitable display, such as display 148, to provide a visual indicator as to the intensity of the forces being applied by the feet of the person being tested. Display 148 is advantageously an analog, light-emitting diode display well known in the art. A preferred display 148 is connected as shown in FIG. 13C using resistors R45, R46, and R47 and capacitor C12. An on-off switch S3 is advantageously used to control power supply to display 148. A reset switch 52 can be used to reset counters 142.

FIG. 13B also shows inverter 151 connected to the output from inverting AND gate 141. The output from inverter 151 is input to OR gate 152, which is also connected to the output of inverter 153. The output of inverter 153 is normally low because the input is normally high because of the application of V+ through resistor R36. The output from OR gate 152 is input to NAND gate 155 which is configured together with NAND gate 156 to form an R-S flip flop. The other input to NAND gate 156 is from the most significant bit of counters 142. Output from NAND gate 156 is connected through resistor R34 to the base of transistor Q1. The emitter of Q1 is connected to ground and the collector is connected to light emitting diode LED1. Light LED1 is powered by positive voltage through resistor r33. Light LED1 is used to indicate when counters 142 have reached a maximum value and overflow can or has occurred.

The output from NAND gate 155 is connected to the cathode diode D7. The anode of D7 is connected to a power source V+ through resistor R35. The anode of D7 is also connected to inverters 161 and 162 in series. The output from inverter 161 is connected to counters 142 in order to hold the count at the highest count possible during overflow conditions. The output of inverter 162 is connected to capacitor C3 which is further connected to the anode of diode D7.

Underflow conditions are similarly held at zero by an analogous circuit to the overflow circuit described above. The underflow circuit includes resistor R37 which is connected to capacitor C4, the input of inverter 182, and the anode of diode D9. The cathode of diode D9 is connected to the borrow terminal of counters 142 to detect the count at a minimum value of zero. The output from inverter 183 is connected to NAND gate 181. The other input to NAND gate 181 is normally held high by V+ through resistor R36. If the output of inverter 183 or reset switches S2 or S3 are activated, then the output from NAND gate 181 goes high and resets counters 142, preventing underflow.

The circuitry described can be reproduced and constructed so as to form a multichannel circuit useful for measuring foot force or pressure from both feet for recording or real time display.

The apparatuses of this invention are used by assemblying the parts together and attaching the foot force detector apparatus such as 20, 70 or 200 onto the feet in the well known fashion. The piezoelectric sensors such as 45 are connected to an appropriate signal amplification and integration circuit such as described above. The force detector apparatus is calibrated using a known applied force prior to mounting. The entire system is preferably battery powered, so that all parts can be used during free motion.

The force sensing shoes described above according to this invention can be utilized by first having a human subject insert his or her foot thereinto and tightening any laces or other suitable fasteners used to retain the shoes on the person's foot. The connectors included on the sensor wires are then connected to the electronic integrating circuitry described. The subject is then able to walk, run, trot or otherwise move in order to generate desired information about the amount of force, types of force, distribution of force and timing of force application.

The novel insole according to this invention is used in a similar manner to the shoes just described except that the insole is placed within a shoe and the wires are run through the ankle opening of the shoe. In either case, small preamplification units consisting of the current-to-voltage converter 120 can be mounted to the wearer's ankle using any sort of suitable device such as an elastic band, adhesive tape or other means. Electrical conductors are then run from the preamplifying current-to-voltage converters for each sensor channel to remaining portions of the circuit as shown in FIGS. 12 and 13A-13C.

Figure 11:
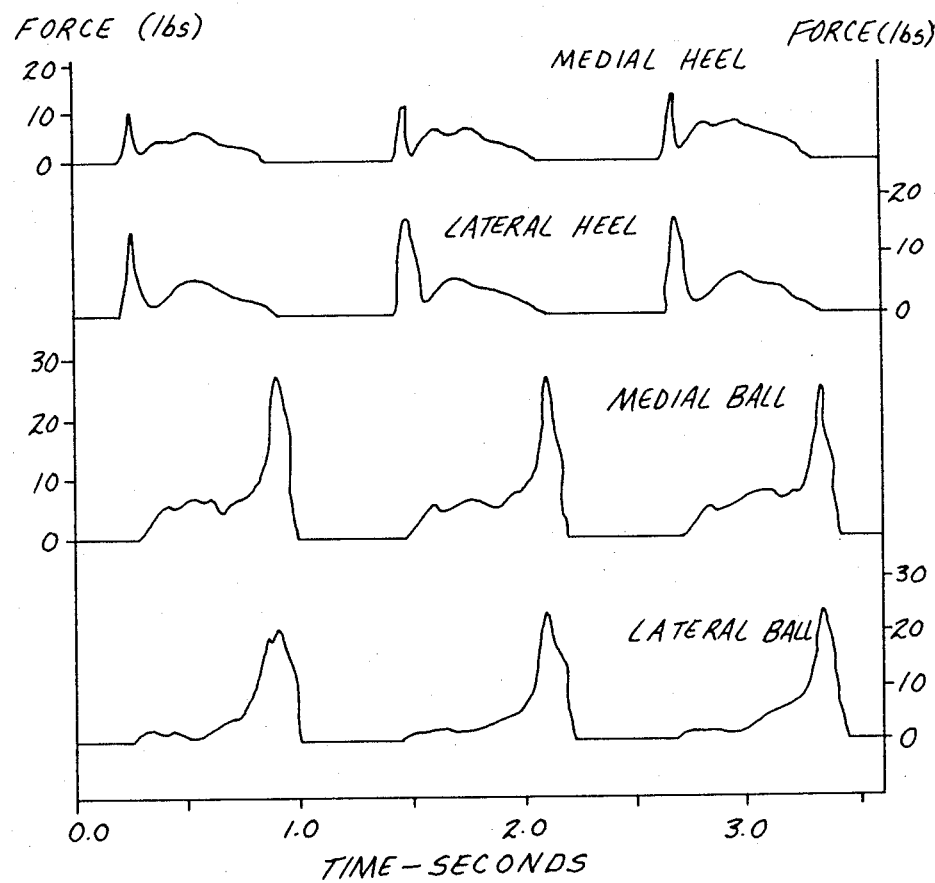
FIG. 11 includes graphs of foot force with time for four sensors such as used in any of the described embodiments.

FIG. 11 shows four graphs indicating experimentally determined levels of force at medial and lateral ball and heel positions such as shown and described above. The detection and recording of the intensity, relative distribution and timing can aid in various treatments, research projects and design efforts.

The preferred embodiments of the inventions described above and other devices according to this invention are advantageously made using well-known techniques for molding, cutting and otherwise forming the indicated materials of construction and assembling them togeyther in the form disclosed. Electronic componentry is also constructed according to well-known construction and manufacturing techniques.

In compliance with the statute, the invention has been described in language more or less specific as the structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

TABLE I

| | VALUE |
|---|---|
| RESISTORS | |
| R2 | 470 ohm |

TABLE I-continued

| | VALUE |
|---|---|
| R3 | 1 megaohm |
| R4 | 1 megaohm |
| R5 | 1 megaohm |
| R6 | 10 kilohm |
| R7 | 10 kilohm |
| R8 | 100 kilohm |
| R9 | 1 kilohm |
| R10 | 1 megaohm |
| R11 | 1 megaohm |
| R12 | 20 kilohm |
| R13 | 20 kilohm |
| R14 | 20 kilohm |
| R15 | 10 kilohm |
| R16 | 20 kilohm |
| R17 | 20 kilohm |
| R18 | 10 kilohm |
| R19 | 2.2 kilohm |
| R20 | 20 kilohm |
| R21 | 2.2 kilohm |
| R22 | 0.91 megaohm |
| R23 | 10 kilohm |
| R24 | 2 kilohm |
| R25 | 10 kilohm |
| R27 | 1 kilohm |
| R28 | 1 megaohm |
| R29 | 10 kilohm |
| R31 | 4.7 kilohm |
| R32 | 4.7 kilohm |
| R33 | 1 kilohm |
| R34 | 10 kilohm |
| R35 | 2.2 kilohm |
| R36 | 10 kilohm |
| R37 | 2.2 kilohm |
| R38 | 50 kilohm |
| R39 | 10 megaohm |
| R40 | 39 kilohm |
| R41 | 10 megaohm |
| R42 | 20 kilohm |
| R43 | 3.9 megaohm |
| R44 | 20 kilohm |
| R45 | 68 ohm |
| R46 | 10 kilohm |
| R47 | 47 kilohm |
| R49 | 1 megaohm |
| CAPACITORS | |
| C1 | 0.068 microfarads |
| C2 | 0.1 microfarads |
| C3 | 300 picofarads |
| C4 | 300 picofarads |
| C5 | 0 01 microfarads |
| C6 | 0.003 microfarads |
| C7 | 0.01 microfarads |
| C12 | 3.3 microfarads |
| C29 | 0.01 microfarads |

We claim:

1. A human foot force sensor assembly for mounting adjacent to plantar surfaces of a human foot to provide electrical signals indicating force experienced at at least one sensor location on the assembly when worn by human subject, comprising:
   backup plate mans adapted to extend over portions of a plantar surface of a human foot; said backup plate means including at least one sensor mounting section which is connected to at least one adjacent remaining portion of said backup plate means using a flexion joint connecting said sensor mounting section to the adjacent remaining portion of said backup plate means; and
   at least one piezoelectric sensor means adapted for connection to said backup plate means at said at least one sensor mounting section.

2. A human foot force sensor assembly according to claim 1 wherein the backup plate means is adapted to extend over substantially all plantar surfaces of a human foot.

3. A human foot force sensor assembly according to claim 1 wherein the backup plate means is adapted to extend over only a limited portion of plantar surfaces of a human foot.

4. A human foot force sensor assembly according to claim 1 wherein the backup plate means is provided with at least one stress isolation slot which extends through a thickness of the backup plate means to define at least portions of the flexion joint.

5. A human foot force sensor assembly according to claim 4 wherein there are a plurality of stress isolation slots.

6. A human foot force sensor assembly according to claim 1 wherein the backup plate means is provided with at least one stress isolation groove which extends partially through a thickness of the backup plate means to define at least portions of the flexion joint.

7. A human foot force sensor assembly according to claim 6 wherein the backup plate means is provided with a plurality of stress isolation grooves.

8. A human foot force sensor assembly according to claim 1 wherein there are a plurality of stress isolation means extending transversely to a medial line running longitudinally along the backup plate means to provide flexibility of the backup plate for relatively natural foot fall contact with a walking surface.

9. A human foot force sensor assembly according to claim 1 wherein at least one stress isolation means extends longitudinally along the backup plate means to provide side-to-side flexibility of the backup plate for relatively natural foot fall contact with a surface.

10. A human foot force sensor assembly according to claim 1 wherein the backup plate means and at least one piezoelectric sensor means are adapted to detachably mount at least one piezoelectric sensor means to the backup plate means.

11. A human foot force sensor assembly according to claim 10 wherein the piezoelectric sensor means is mounted in an insert adapted for detachable reception in a receptacle formed by a sole assembly.

12. A plurality of human foot force sensor assemblies in accordance with claim 1 joined in a shoe means.

13. A plurality of human foot force sensor assemblies according to claim 1 joined in a shoe means and positioned to detect force applied through the metatarsal or ball of the human foot and at the heel of the human foot.

14. A human foot force sensor assembly according to claim 1 and further defined by said piezoelectric sensor means being adapted to generate a piezoelectric signal only as a result of force components applied approximately normal to a ground directed surface of the backup plate means sensor mounting section.

15. A human foot force sensor assembly according to claim 1 wherein the piezoelectric sensor means is a poled ceramic piezoelectric element.

16. A human foot force sensor assembly according to claim 1 wherein the piezoelectric sensor means is oriented with poled sensor faces thereof approximately parallel to ground directed and foot directed surfaces of the backup plate means.

17. A human foot force sensor assembly according to claim 1 wherein the piezoelectric sensor means is surrounded at lateral sides thereof by an elastic material for mechanically restraining the piezoelectric sensor means against lateral motion.

18. A human force sensor assembly according to claim 1 wherein the piezoelectric sensor means includes a protective cap.

19. A human force sensor assembly according to claim 1 and further comprising resilient sole pad means attached to a ground directed side of the backup plate means.

20. A human foot force sensor assembly according to claim 1 wherein at least one piezoelectric sensor means is provided with means for supporting and distributing forces over the poled faces of at least one piezoelectric sensor element.

21. A human force sensor assembly according to claim 20 wherein there are means for supporting and distributing forces over both poled faces of at least one piezoelectric sensor element.

22. A human foot force sensor assembly according to claim 20 wherein said means for supporting and distributing forces is compressionally more resilient than the at least one piezoelectric sensor element.

23. A human force sensor assembly according to claim 21 wherein said means for supporting and distributing forces are compressionally more resilient than the at least one piezoelectric sensor element.

24. A human foot force sensor assembly according to claim 23 and wherein the piezoelectric sensor element is mounted within a sole pad means which is more resilient than the piezoelectric sensor element and the means for supporting and distributing forces over the poled faces of the piezoelectric sensor means.

25. A human foot force sensor assembly according to claim 22 and wherein the piezoelectric sensor element is mounted within a sole pad means which is more resilient than the piezoelectric sensor element and the means for supporting and distributing forces over the poled faces of the piezoelectric sensor means.

26. A human foot force detection system including at least one human foot force sensor assembly according to claim 25 and further comprising:
   electric conductors connected to at least one piezoelectric sensor element; and
   a charge amplification and integration circuit for amplifying, integrating and outputting usable information from the output signal of the piezoelectric sensor element which is indicative of force applied through the piezoelectric sensor element.

27. A human foot force detection system including at least one human foot force sensor assembly according to claim 1 and further comprising:
   electrical conductors connected to at least one piezoelectric sensor element; and
   a charge amplification and integration circuit for amplifying, integrating and outputting usable information from the output signal of the piezoelectric sensor element which is indicative of force applied through the piezoelectric sensor element.

28. A human foot force detection system according to claim 27 and wherein the charge flow amplification and integration circuit includes:
   routing means connected to said electrical output means of said means for detecting whether said voltage signal is positive or negative, and for routing the frequency variable signal to appropriate portions of the digital counter means;
   anti-jitter means for requiring at least two consistent-polarity cycles in the frequency variable signal prior to change of said digital counter means from a positive cycle counting mode to a negative cycle counting mode, or vice-versa.

29. A human foot force sensor shoe assembly for being worn on a human foot to provide electrical signals indicating force experienced at at least one sensor location thereon, comprising:
   a shoe means;
   at least one backup plate means adapted for connection to the shoe means to receive force from plantar surfaces of a human foot; said backup plate means including at least one sensor mounting section which is connected to at least one adjacent remaining portion of said backup plate means using a flexion joint connecting said sensor mounting section to the adjacent remaining portion of said backup plate means; and
   at least one piezoelectric sensor means adapted for connection to said backup plate means at said at least one sensor mounting section.

30. A human foot force sensor shoe assembly according to claim 29 wherein the shoe means is adapted to detachably mount the backup plate means.

31. A human foot force sensor shoe according to claim 29 wherein the shoe means is provided with at least one sensor assembly which is supported by a backup plate means and at least one piezoelectric sensor means.

32. A human foot force sensor shoe according to claim 31 and further comprising at least one sensor assembly receptacle formed in said shoe means for receiving at least one sensor assembly.

33. A human foot force sensor shoe according to claim 32 wherein the sensor assembly receptacle is open at a side of said shoe means.

34. A human foot force sensor shoe according to claim 32 wherein the sensor assembly receptacle is open at a ground directed surface of said shoe means.

35. A human foot force sensor shoe according to claim 31 wherein the shoe means is provided with at least two sensor assembly receptacles for detachably mounting sensor assemblies at the metatarsal or ball and at the heel of the foot.

36. A human foot force sensor shoe according to claim 35 wherein the sensor assembly receptacle is open at a side of said shoe means.

37. A backup plate means adapted for mounting adjacent to plantar surfaces of a human foot to support and position at least one piezoelectric sensor means, comprising at least one sensor mounting section which is connected to at least one adjacent remaining portion of said backup plate means using a flexion joint connecting said sensor mounting section to the adjacent remaining portion; said sensor mounting section being substantially rigid at least adjacent to a sensor mount which is adapted to mount a piezoelectric sensor thereto and provide support thereof and distribute forces mroe equally over the sensor means.

38. A backup plate means according to claim 37 wherein the flexion joint is constructed to integrally connect substantially rigid portions of the at least one sensor mounting section to the at least one adjacent remaining portion of the backup plate means.

39. A backup plate means according to claim 37 which is adapted to extend over substantially all plantar surfaces of a human foot.

40. A backup plate means according to claim 37 which is adapted to extend over only a limited portion of plantar surfaces of a human foot.

41. A backup plate means according to claim 37 which is provided with at least one stress isolation slot which extends through a thickness of the backup plate means to define at least portions of the flexion joint.

42. A backup plate means according to claim 37 which is provided with at least one stress isolation groove which extends partially through a thickness of the backup plate.

43. A backup plate means according to claim 37 wherein the backup plate means is adapted to detachably mount a piezoelectric sensor means.

44. A backup plate means according to claim 37 wherein the backup plate means is adapted to detachably mount a piezoelectric sensor means including an enlarged flange which fits in an elastic interiorly enlarged receptacle.

45. A human foot force sensor insole adapted to mount within a shoe means along plantar portions of a human foot comprising a flexible mat of elastic material adapted to receive at least one piezoelectric transducer in a detachable retaining interrelationship, and means for supporting and distributing force over the piezoelectric transducer to provide relatively uniform stress thereover.

46. A human foot force sensor insole according to claim 45 wherein the retaining interrelation is provided by a receptacle which is enlarged at a point within the receptacle to define an outer flange.

47. A human foot force sensor insole according to claim 45 and further comprising a piezoelectric sensor means.

48. A human foot force sensor insole according to claim 46 and further comprising a piezoelectric sensor means.

49. A human foot force sensor insole according to claim 48 wherein the piezoelectric sensor means is provided with a retaining flange which is receivable within the receptacle.

50. A human foot force sensor insole according to claim 49 wherein the piezoelectric sensor means is disk shaped and has a disk shaped retaining flange.

51. A piezoelectric sensor insert for use in human foot force sensor assemblies, comprising:
    at least one piezoelectric sensor element having poled faces for receiving applied forces therethrough;
    means for supporting and distributing force over the piezoelectric transducer to provide relatively uniform stress thereover; said means for supporting and distributing force being relatively more resilient than said piezoelectric sensor element;
    an insert piece laterally supporting the piezoelectric sensor element; said insert piece being relatively more resilient than said means for supporting and distributing force.

52. A piezoelectric sensor insert according to claim 51 wherein there are means for supporting and distributing force at opposing poled faces of the piezoelectric sensor element.

53. A piezoelectric sensor insert according to claim 52 and further comprising a ground contacting face piece.

54. A piezoelectric sensor insert according to claim 53 wherein the at least one piezoelectric sensor element, means for supporting and distributing force, and ground contacting face piece are bonded together in a unit.

55. A piezoelectric sensor insert according to claim 52 and further comprising backup plate means.

* * * * *